United States Patent
Lange et al.

(10) Patent No.: US 7,355,082 B2
(45) Date of Patent: Apr. 8, 2008

(54) METHOD OF PURIFYING LONG-CHAIN ALKYL PHENOLS AND MANNICH ADDUCTS THEREOF

(75) Inventors: Arno Lange, Bad Dürkheim (DE); Hans Peter Rath, Grünstadt (DE); Marc Walter, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 415 days.

(21) Appl. No.: 10/475,214

(22) PCT Filed: Apr. 22, 2002

(86) PCT No.: PCT/EP02/04415

§ 371 (c)(1), (2), (4) Date: Oct. 20, 2003

(87) PCT Pub. No.: WO02/086037

PCT Pub. Date: Oct. 31, 2002

(65) Prior Publication Data

US 2004/0133048 A1    Jul. 8, 2004

(30) Foreign Application Priority Data

Apr. 23, 2001 (DE) .................................. 101 19 738

(51) Int. Cl.
*C07C 37/68* (2006.01)
*C07C 37/82* (2006.01)

(52) U.S. Cl. ..................................................... 568/749
(58) Field of Classification Search ................ 568/479, 568/749

See application file for complete search history.

(56) References Cited

U.S. PATENT DOCUMENTS 3,368,972 A * 2/1968 Otto ............................ 508/558
3,904,595 A    9/1975 Plonsker et al.
4,101,590 A * 7/1978 Sato et al. ................... 568/750

FOREIGN PATENT DOCUMENTS

NL      7712270     * 11/1977

OTHER PUBLICATIONS

Chem. Rev., Reichardt, 1994, vol. 94, pp. 2319-2358.*
Additive für Ottokraftstoffe, Rossenbeck, 223-229, 1978.

* cited by examiner

*Primary Examiner*—Yvonne Eyler
*Assistant Examiner*—Kellette Gale
(74) *Attorney, Agent, or Firm*—Novak Druce + Quigg LLP

(57) ABSTRACT

A process for purifying a phenol derivative selected from alkylphenols having a number average molecular weight of from 200 to 4 000 and Mannich adducts thereof is described, in which the phenol derivative is brought into intimate contact with an extracting agent having a polarity $E_T(30)$ of from 57 to 38 kcal/mol, a phase containing the phenol derivative and an extracting agent phase are allowed to separate from one another and the extracting agent phase is removed.

9 Claims, No Drawings

METHOD OF PURIFYING LONG-CHAIN ALKYL PHENOLS AND MANNICH ADDUCTS THEREOF

The present invention relates to a process for purifying alkylphenols having a number average molecular weight of from 200 to 4 000 and Mannich adducts thereof.

Aminoalkylated polyalkylenephenols, as obtainable by Mannich reaction of amines and aldehydes with polyalkylene-substituted phenols, play an important role as fuel additives for keeping valves and carburetors or injection systems of gasoline engines clean (cf. for example M. Rossenbeck in Katalysatoren, Tenside, Mineralöladditive, Editors J. Falbe, U. Hasserodt, page 223, G. Thieme Verlag, Stuttgart 1978).

The crude reaction products of the Mannich reaction often exhibit varying cleaning effects and have a number of disadvantages. Owing to the complicated composition of the mixtures, a dark color and an intense odor are often observed, adversely affecting the customer acceptance. Furthermore, the viscosity at low temperatures is often too high, which may lead to sticking of the valves. This is understood as meaning complete loss of compression on one or more cylinders of the internal combustion engine when the spring forces are no longer sufficient to close the valves properly.

The undesired properties are often caused by byproducts and low molecular weight fractions which originate from the preparation of the alkylphenol. The alkylphenols used as starting material are generally prepared by alkylating phenol with polyolefins, such as polyisobutene. In the alkylation with polyisobutene, a reduction in the molecular weight, i.e. partial cleavage of the polyisobutene chain, is often observed. The isobutene eliminated can form lower alkylphenols such as tert-butylphenol or tert-octylphenol.

Moreover, troublesome byproducts may form in the Mannich reaction, in particular with primary amines and formaldehyde.

It is an object of the present invention to provide a simple process for removing byproducts and low molecular weight fractions from long-chain alkylphenols and the Mannich adducts thereof.

We have found that this object is achieved, according to the invention, by a process for purifying a phenol derivative selected from alkylphenols having a number average molecular weight of from 200 to 4 000 and Mannich adducts thereof, in which the phenol derivative is brought into intimate contact with an extracting agent having a polarity $E_T(30)$ of from 57 to 38, preferably from 56 to 48, kcal/mol, a phase containing the phenol derivative and an extracting agent phase are allowed to separate from one another and the extracting agent phase is removed.

On the one hand, an alkylphenol can be subjected to the novel process; the purified alkylphenol can then be reacted to give a Mannich adduct, as described further below. Alternatively, a crude alkylphenol can be reacted to give a Mannich adduct and the latter can be purified by the novel process.

The phenol derivative can be subjected as such, i.e. in the absence of a solvent, to the novel process. In order to reduce the viscosity, it is advantageous in many cases to dissolve the phenol derivative in a nonpolar solvent, i.e. one having a polarity $E_T(30)$ of from 35 to 30, and to bring the solution into contact with the extracting agent. The nonpolar solvent and the amount of the nonpolar solvent relative to the phenol derivative are chosen so that the solution of the phenol derivative and the extracting agent are not completely miscible at the temperature at which the novel process is carried out. In other words, they have a miscibility gap, so that spontaneous separation into a polar phase containing phenol derivative and an extracting agent phase takes-place after they are brought into-contact. Suitable nonpolar solvents are aliphatic or aromatic hydrocarbons, such as n-pentane, n-hexane, n-heptane, n-octane and isomers thereof, petroleum ether, naphtha, benzene, toluenes, xylenes and commercial solvent mixtures, such as Solvesso® or Aromatics®150, and mixtures thereof.

The solution generally contains at least 5, mostly from 20 to 90, % by weight of phenol derivative.

Since such solvents are also used in the preparation of the phenol derivatives, the crude reaction mixture, too, can be subjected directly to the extraction.

In the novel process, a solvent having a polarity $E_T(30)$ of from 57 to 38, preferably from 56 to 48, kcal/mol is used as the extracting agent. The determination of the solvent polarity on the basis of the $E_T(30)$ scale is described in Liebigs Ann. Chem. (1983), 721-743, which is hereby incorporated by reference in its entirety. It was found that solvents of said polarity have a high dissolving power for the byproducts and low molecular weight fractions but are not miscible with the phenol derivative, so that they form a separate phase in which the byproducts and low molecular weight fractions accumulate and from which they can be readily removed. If, on the other hand, the polarity of the extracting agent is lower than stated, there is no satisfactory phase separation with the phenol derivative. If the polarity is higher than stated, the dissolving power of the extracting agent for the component to be removed is insufficient.

Depending on the type of extracting agent used and on the alkyl chain length of the alkylphenol or its Mannich adduct, the extracting agent phase or the phase containing phenol derivative is the heavier phase. The extracting agent phase separating out is generally evident from the intense dark color which is due to the extracted colored byproducts.

Extracting agents suitable for the novel process belong in particular to the classes consisting of the alcohols, such as methanol, ethanol n-propanol or isopropanol, nitrites, such as acetonitrile, ketones, such as acetone or butanone, or esters, such as ethyl acetate or butyl acetate, lactones, such as butyrolactone, and amides, such as formamide or dimethylformamide. Preferred extracting agents are methanol, ethanol, n-propanol, isopropanol, acetone and butanone.

Mixtures of the solvents with one another or with water are also suitable, for example in an amount of up to 20% by weight. A suitable extracting agent is, for example, methanol with 10% by weight of water.

In general, from 1 to 200, preferably from 20 to 100, parts by weight of extracting agent are used per 100 parts by weight of phenol derivative or a solution thereof in a nonpolar solvent.

The components may be brought into contact continuously or batchwise. A plurality of batchwise operations may be carried out in succession in a cascade-like manner, the phase containing phenol derivative and separated from the extracting agent phase being brought in each case into contact with a fresh portion of extracting agent. For the batchwise procedure, the phenol derivative or its solution in a nonpolar solvent and the extracting agent are brought into contact in a suitable vessel with mechanical agitation, for example by stirring or shaking, the mixture is left to stand for phase separation and one of the phases is removed by expediently withdrawing the heavier phase at the bottom of the vessel.

For the continuous procedure, the extracting agent is preferably passed countercurrently to the phenol derivative in an extraction zone. Vertically arranged separation columns which are usually provided with packings or moving or stationary internals are advantageously used for this purpose. The heavy phase is preferably fed in in the upper region of the separation column and the lighter phase in the lower region of the separation column and said phases are thus passed countercurrently to one another. The light phase settles out at the top of the separation column on the heavier one and can be removed by means of an overflow pipe. The heavy phase collects at the bottom of the separation column and can be removed, preferably via a riser. Alternative embodiments of a continuous liquid-liquid extraction are known to a person skilled in the art.

While being brought into contact, the phase containing phenol derivative may be divided and the extracting agent phase undivided, or vice versa.

The success of the novel purification process can be monitored, particularly in the case of a continuous or cascade procedure, if the concentration of the extracted components is determined in the spent extracting agent. This can be effected by measuring the density or refractive index. IR or UV-VIS spectroscopy procedures, if necessary as an on-line method, can also be used. The purification-process can be stopped, for example, when the concentration has fallen below a predetermined value. The spent extracting agent can be worked up, for example by distillation or membrane methods. Here, it can be separated into unconverted starting materials, such as phenols, which can be recycled to the preparation process, and byproducts, which are discarded. As a result of the novel process, the concentration of byproducts and low molecular weight fractions in the phenol derivative can be reduced by a factor of more than 10, in particular more than 20, in a simple manner.

The novel process is carried out in general at from 0 to 120° C., preferably from 10 to 60° C., for example at room temperature. Atmospheric pressure is generally employed, operation at superatmospheric pressure also being possible.

Alkylphenols which can be purified by the novel process are generally obtained by reacting a phenol with a substantially monounsaturated olefin of suitable chain length in the presence of an alkylation catalyst. Suitable phenols are (unsubstituted) phenol itself and substituted phenols. The substituted phenols preferably have, in addition to the hydroxyl group, one or two further substituents, which are preferably ortho to the hydroxyl group. Suitable substituents are, for example, $C_1$-$C_4$-alkyl and $C_1$-$C_4$-alkoxy. Phenol, 2-methylphenol and 2-ethylphenol are particularly preferred.

Particularly suitable substantially monounsaturated olefins are oligomerization or polymerization products of propene, butene or isobutene. Polyisobutenes are most particularly preferred, especially highly reactive polyisobutenes which contain more than 80, in particular more than 90, mol % of isobutene units. The polyisobutenes preferably have a number average molecular weight of from 500 to 1 500 and a polydispersity of from 1.1 to 5.0, preferably less than 1.9. Polydispersity is understood as meaning the quotient of the weight average molecular weight $M_w$ and of the number average molecular weight $M_n$.

The alkylation is suitably effected at from −10 to 80° C., preferably from 0 to 40° C. Suitable alkylation catalysts are protic acids, such as sulfuric acid, phosphoric acid and organic sulfonic acids, e.g. trifluoromethanesulfonic acid; Lewis acids, such as aluminum trihalides, e.g. aluminum trichloride or aluminum tribromide, boron trihalides, e.g. boron trifluoride and boron trichloride, tin halides, e.g. tin tetrachloride, titanium halides, e.g. titanium tetrabromide and titanium tetrachloride, and iron halides, e.g. iron trichloride. Lewis acid alkylation catalysts can be used in combination with electron donors, such as alcohols, in particular $C_1$-$C_6$-alkanols, phenols or ethers. Boron trifluoride etherate and boron trifluoride phenolate are particularly preferred.

Suitable solvents for the alkylation are hydrocarbons, in particular aliphatic hydrocarbons, such as pentane, hexane and heptane, petroleum naphthas boiling within a range from 35 to 100° C., dialkyl ethers, e.g. diethyl ether, and halogenated hydrocarbons, such as dichloromethane or trichloromethane. Aromatics, such as toluene, xylene and isomers thereof, can also be used.

For the preparation of the Mannich adducts, the alkylphenol is reacted with an aldehyde and a primary or secondary amine. Suitable processes are described, for example, in U.S. Pat. No. 4,231,759; U.S. Pat. No. 4,117,011; U.S. Pat. No. 5,634,951; U.S. Pat. No. 5,725,612; GB 1,368,532 or the prior applications DE 199 48 114.8 and DE 199 48 111.3.

A preferably reacted aldehyde is formaldehyde. Suitable formaldehyde sources are aqueous formaldehyde solution and formaldehyde oligomers, such as trioxane and paraformaldehyde.

Suitable primary amines are, for example, methylamine, ethylamine, n-propylamine, isopropylamine, dimethylaminopropylamine, aniline and benzylamine. Suitable secondary amines are dimethylamine, diethylamine, piperidine, morpholine and piperazine. Alkylenediamines, dialkylenetriamines, trialkylenetetramines and polyalkylenepolyamines, such as oligo- or polyalkyleneimines, in particular oligo- or polyethyleneimines, preferably those of 2 to 20 ethyleneimine units, are furthermore suitable. The reaction products of alkylene oxides, in particular ethylene oxide, with primary amines are also suitable.

The water of reaction formed in the Mannich reaction can be removed by heating in the presence of an entraining agent. Suitable entraining agents are benzene, toluene, xylene and mixtures thereof.

Alkylphenol, aldehyde and amine are preferably used in a molar ratio of from 1:0.5:0.5 to 1:4:4.

Although a very wide range of alkylphenols and Mannich adducts thereof can be purified by the novel process, it is particularly suitable for 4-polyisobutenylphenol and Mannich adducts thereof.

The Mannich adduct purified by the novel process or a Mannich adduct prepared from a phenol derivative purified by the novel process is suitable as a surfactant or surface-active substance, for example as a detergent additive in fuel and lubricant compositions, if required in combination with further conventional fuel and lubricant additives.

Examples of such additional components are polyalkenemonoamines, polyalkenepolyamines, nitropolyisobutanes, hydroxynitropolyisobutanes, copolymers of $C_2$-$C_{40}$-olefins with maleic anhydride in which one or both carboxyl groups have been neutralized, alkyl sulfosuccinates and salts thereof, tridecanol butoxylates, isotridecanol butoxylates, isononylphenol butoxylates, adipates, phthalates, isophthalates, terephthalates and trimellitates of isooctanol, of isononanol, of isodecanol and of isotridecanol, polypropylene oxide and polybutylene oxide and derivatives thereof.

The examples which follow illustrate the invention.

EXAMPLE 1

1 200 g of 4-polyisobutenylphenol ($M_n$ of polyisobutene=1 000) in 500 ml of xylene were refluxed with 97 g of formaldehyde solution (37% by weight) and 135 g of dimethylamine solution (40% by weight) for 3 hours with removal of water. The cooled reaction solution was then stirred with 500 ml of methanol. After the phase separation, the methanol phase was separated off and discarded. This process was repeated twice. The product phase was finally evaporated down in a rotary evaporator at 140° C. and 10 mbar. 1 240 g of 2-(dimethylaminomethyl)-4-polyisobutenylphenol were obtained as a pale oil.

EXAMPLE 2

A Mannich base was prepared as in example 1 from a polyisobutenylphenol ($M_n$ of polyisobutene=1 000), formaldehyde and dimethylamine in a molar ratio of 1:1.1:1.1. The xylene was removed by evaporation (without prior washing with methanol). 100 g of the Mannich base was stirred for 30 minutes with 100 ml of methanol. The product phase was separated off and residual amounts of methanol were removed in a rotary evaporator at 100° C. and 20 mbar. 94 g of purified product were obtained.

In further experiments, instead of the methanol, 100 ml of the solvents below were used with 100 g of Mannich base. The yield of purified product is shown in brackets.

Solvent: Ethanol (91 g), acetone (89 g), ethyl acetate (90 g), dimethylformamide (95 g).

EXAMPLE 3

A 4-polyisobutenylphenol was prepared from 225 g of phenol (dissolved in 130 ml of toluene), 14 g of $BF_3$ phenolate and 1 200 g of polyisobutene ($M_n$=1 000; dissolved in 700 ml of hexane). After the reaction, the crude mixture was extracted with 500 ml of methanol and the methanol phase was separated off. This process was repeated three times. The solution of the polyisobutenylphenol was evaporated down in a rotary evaporator at 140° C. and 10 mbar. 1 250 g of 4-polyisobutenylphenol were obtained as a pale oil. The methanol phases were distilled over a 100 cm long packed column containing stainless steel wire mesh coils, the following fractions being obtained: 1 400 g of methanol (from 64 to 68° C., 950 mbar); 105 g of phenol (from 69 to 72° C., 12 mbar); and 5 g of $BF_3$-methanol complex (from 76 to 80° C., 12 mbar).

We claim:

1. A process for purifying a phenol derivative selected from polyisobutenyl phenols having a number average molecular weight of from 200 to 4 000 or Mannich adducts thereof, in which the phenol derivative is brought into intimate contact with an extracting agent having a polarity $E_T(30)$ of from 57 to 38 kcal/mol wherein the extracting agent is selected from methanol, ethanol and mixtures thereof, a phase containing the phenol derivative and an extracting agent phase are allowed to separate from one another and the extracting agent phase is removed.

2. A process as claimed in claim 1, wherein the extracting agent has a polarity $E_T(30)$ of from 56 to 48 kcal/mol.

3. A process as claimed in claim 1, in which the phenol derivative is dissolved in a solvent having a polarity $E_T(30)$ of from 35 to 30 kcal/mol and the solution is brought into contact with the extracting agent.

4. A process as claimed in claim 1, in which the polyisobutenyl phenol has a number average molecular weight of from 500 to 1 500.

5. A process as claimed in claim 1, wherein the Mannich adduct is the reaction product of the polyisobutenyl phenol with formaldehyde and a primary or secondary amine.

6. A process as claimed in claim 1, in which the polyisobutenyl phenol is a 4-polyisobutenylphenol.

7. A process as claimed in claim 1, in which the extracting agent is passed countercurrently to the phenol derivative in an extraction zone.

8. A process for purifying a phenol derivative selected from polyisobutenyl phenols having a number average molecular weight of from 200 to 4 000 or Mannich adducts thereof, in which the phenol derivative is brought into intimate contact with an extracting agent having a polarity $E_T(30)$ of from 57 to 38 kcal/mol wherein the extracting agent is methanol, a phase containing the phenol derivative and an extracting agent phase are allowed to separate from one another and the extracting agent phase is removed.

9. A process for purifying a phenol derivative selected from polyisobutenyl phenols having a number average molecular weight of from 200 to 4 000 or Mannich adducts thereof, wherein the polyisobutenyl phenols are obtained by reacting a phenol with a substantially monounsaturated olefin in the presence of an alkylation catalyst, in which the phenol derivative is brought into intimate contact with an extracting agent having a polarity $E_T(30)$ of from 57 to 38 kcal/mol wherein the extracting agent is selected from methanol, ethanol and mixtures thereof, a phase containing the phenol derivative and an extracting agent phase are allowed to separate from one another and the extracting agent phase is removed.

* * * * *